United States Patent [19]

Isomura et al.

[11] Patent Number: 4,970,335
[45] Date of Patent: Nov. 13, 1990

[54] (CYCLOALKYLAMINO)METHYLENEBIS(PHOSPHONIC ACID)

[75] Inventors: Yasuo Isomura; Makoto Takeuchi; Shuichi Sakamoto, all of Tokyo; Tetsushi Abe, Saitama, all of Japan

[73] Assignee: Yamanouchi Pharmaceutical Co., Ltd., Tokyo, Japan

[21] Appl. No.: 300,350

[22] Filed: Jan. 23, 1989

[30] Foreign Application Priority Data

Jan. 20, 1988 [JP] Japan ................................. 63-11656

[51] Int. Cl.$^5$ ............................................... C07F 9/02
[52] U.S. Cl. ...................................... 562/13; 558/158
[58] Field of Search .................... 562/13; 558/158; 514/102

[56] References Cited

U.S. PATENT DOCUMENTS 3,846,420 11/1974 Wollmann et al. .................... 562/13
3,957,160 5/1976 Ploger et al. .......................... 562/13

Primary Examiner—Cecilia Shen
Attorney, Agent, or Firm—Burgess, Ryan & Wayne

[57] ABSTRACT (Cycloalkylamino)methylenebis(phosphonic acid) represented by the general formula:

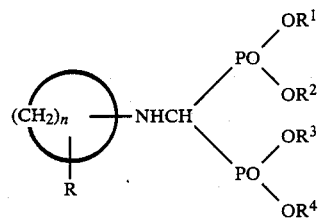

in which, R, $R^1$, $R^2$, $R^3$ and $R^4$ represent a hydrogen atom or a lower alkyl group, and n represents an integer from 3 to 10, a lower alkyl ester thereof or a pharmaceutically acceptable salt thereof; and a bone-resorption inhibitor and an anti-arthritis containing the same.

2 Claims, No Drawings

(CYCLOALKYLAMINO)METHYLENEBIS(PHOSPHONIC ACID)

BACKGROUND OF THE INVENTION

1. Field of the Invention

The present invention relates to (cycloalkylamino)-methylenebis(phosphonic acid), lower alkyl ester thereof or pharmaceutically acceptable salts thereof which are useful as medicines having a bone resorption inhibitory effect as well as an anti-inflammatory effect and an antirheumatic effect and also relates to medicines containing the compounds as an active ingredient.

2. Description of the Related Art

Some derivatives of (cycloalkylamino)methylenebis(phosphonic acid) are known. Japanese patent laid-open No. 37,829/79 discloses compounds having an unsubstituted cyclopentyl group or a cyclohexyl group and Japanese patent publication No. 12,319/80 discloses a compound having a cyclohexyl group as the cycloalkyl group respectively. These Japanese patent gazettes mention that these compounds can be used as agricultural chemicals, especially as herbicide and that they can be use in a method for preventing precipitation in water or in aqueous solution, but are quite silent on the usability of the compounds as medicines.

An object of the present invention is to provide (cycloalkylamino)methylenebis(phosphonic acid) derivatives having unsubstituted or substituted cycloalkyl group having 3 to 10 carbon atoms and are useful for a bone-resorption inhibitor and an anti-arthritis.

SUMMARY OF THE INVENTION

The present invention provides a pharmaceutical composition containing, as an active ingredient, (cycloalkylamino)methylenebis(phosphonic acid) represented by the general formula:

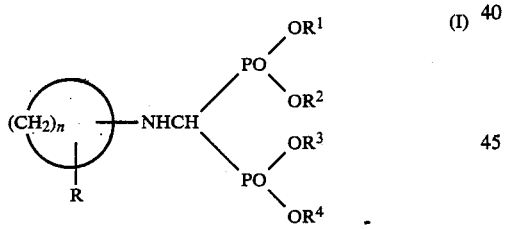

(I)

in which, R, $R^1$, $R^2$, $R^3$ and $R^4$ represent a hydrogen atom or a lower alkyl group, and n represents an integer from 3 to 10; a lower alkyl ester thereof; or a pharmaceutically acceptable salt thereof.

The present invention provides also a bone-resorption inhibitor and an anti-arthritis containing, as an active ingredient, the compound represented by the general formula (I), a lower alkyl ester thereof or a pharmaceutically acceptable salt thereof.

The present invention provides also a novel compound represented by the general formula (I) in which R, $R^1$, $R^2$, $R^3$ and $R^4$ represent a hydrogen atom or a lower alkyl group, n represents an integer from 3 to 10 but R represents a lower alkyl group when n is 5 or 6, a lower alkyl ester thereof or a pharmaceutically acceptable salt thereof.

The lower alkyl ester in the general formula (I) is a linear or branched hydrocarbon group having 1 to 5 carbon atoms. The typical lower alkyl group is methyl group, ethyl group, propyl group or isopropyl group.

The group represented by a chemical structure:

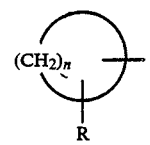

in the general formula (I) represents a cyclopropyl group, a cyclobutyl group, a cyclopentyl group, a cyclohexyl group, a cycloheptyl group, a cyclooctyl group, a cyclononyl group or a cyclodecyl group each of which is substituted by a lower alkyl group or unsubstituted.

The salt of the compound (I) is a salt with pharmaceutically acceptable base. As preferable salts, it can be mentioned salts with inorganic bases such as sodium salts, potassium salts or the like and salts with organic bases such as ammonium salts, triethylamine salts or the like.

Preparation of the compounds

The compounds of the present invention can be prepared in accordance with the following reaction formula:

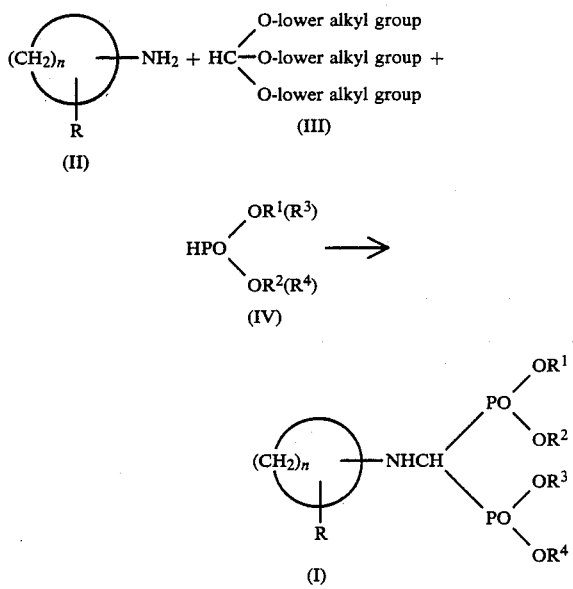

In this reaction, all components of a cycloalkylamine (II), a lower alkyl ortho-formate (III) and a phosphorous acid or its lower alkyl ester (IV) are mixed each in the corresponding reaction amount and are heated. A reaction solvent is not specifically required. The reaction is performed generally at 100° to 200° C., preferably at 150° C. or so, for 10 to 60 minutes.

For isolating and purifying the thus obtained reaction product, for example, the reaction mixture is charged on a silica gel column and eluted with a mixed solvent of methanol-chloroform. In the above mentioned reaction, the corresponding bisphosphonic acid or bisphosphonate can be obtained respectively from the phosphorous acid or its ester (IV).

The bisphosphonates can be converted into the corresponding bisphosphonic acids by hydrolysis. The hydrolysis is generally carried out by heating the bisphosphonates under reflux in a concentrated hydrochloric acid. Alternatively, the bisphosphonates can be treated with a strong acid or a trimethylsilyl halide in a water-free solvent. For the method, in general, a commercial anhydrous hydrobromic acid in acetic acid can be used directly or in a form of a pertinently diluted solution, or a solution of a trimethylsilyl iodide as dissolved in a solvent such as carbon tetrachloride, dimethylformamide, chloroform, toluene, etc. can be used. Regarding the temperature, the hydrolysis is carried out with cooling or heating. For example, when the ester is hydrolyzed with a trimethylsilyl halide with cooling at $-10°$ C. or lower, a partially hydrolyzed product is obtained.

When the bisphosphonic acid is to be converted into its salt, the acid is treated with a base such as sodium hydroxide, potassium hydroxide, ammonia or organic amines, etc. in a conventional manner.

Pharmaceutical use

The compounds (I) and their salts provided by the present invention have a bone resorption-inhibitory action and also have an action for inhibiting hypercalcemia caused by bone resorption. In addition, these are recognized to have excellent anti-inflammatory action and antipyretic and analgesic action.

Experimental test methods and results are mentioned hereunder so as to support the inhibitory effect on hypercalcemia of the compounds (I) and their salts provided by the present invention.

(1) Inhibitory Effect on Hypercalcemia of Rats

Rats of hypercalcemia induced by administration of parathyroid hormone were used, and the decrement of the serum calcium amount by administration of the compound was measured.

Test Method

30 μg/kg of human 1-34 parathyroid hormone, (PTH, manufactured by Peptide Laboratory) which was dissolved in a 0.1% BSA (bovine serum albumin)-containing physiological saline (the contents of the PTH is 6 μg/ml) was intravenously injected in an amount of 30 μg/kg (5 ml/kg as the solution) to 5-week male Wistar rats which had been fasting for 20 hours. Only 0.1% BSA-containing physiological saline was injected to the normal control group in the same manner. 45 minutes after the PTH injection, the rats were etherized and then subjected to celiotomy, whereby the blood was collected from the abdominal cava with a vacuum blood-collecting tube. The blood collected was immediately centrifuged by 3000 rpm, at 4° C. for 10 minutes to isolate the serum. The ionized calcium ($Ca^{++}$) concentration in the serum was immediately measured with a $Ca^{++}$ meter (Sera 250, manufactured by Horiba Manufacturing Co.).

The compounds of the present invention were dissolved using sodium hydroxide and hydrochloric acid, in physiological saline (pH 7.4), for subcutaneous administration, in such amounts that the dose amounted to 2 ml/kg. They were administered 72 hours before the PTH injection. A physiological saline or a distilled water was administered to the normal control group and the control group, in the same manner. As a reference compound, salmon calcitonin (SCT, manufactured by Armour Co.) was used for the measurement. The SCT was subcutaneously administered at the dose of 2 ml/kg 30 minutes before the PTH injection.

The results for each group were expressed in terms of mean ±S.E. (standard error) and comparison was made among the groups by testing by one-way analysis of variance. The significance level was taken at 5%.

Results

The results obtained by the subcutaneous administration are shown in Table 1.

TABLE 1

| | Subcutaneous administration | | |
|---|---|---|---|
| Compound Tested | Dose (mg/kg) | N | Serum $Ca^{++}$ (m mole/l) |
| Normal control | — | 5 | 1.42 ± 0.02 |
| Control | — | 5 | 1.48 ± 0.03 |
| Compound of Example 8 | 0.3 | 5 | 1.25 ± 0.02** |
| Compound of Example 8 | 1.5 | 5 | 1.12 ± 0.02** |
| Normal Control | — | 5 | 1.41 ± 0.02** |
| Control | — | 5 | 1.46 ± 0.02 |
| Compound of Example 15 | 0.03 | 5 | 1.37 ± 0.02** |
| Compound of Example 15 | 0.1 | 5 | 1.20 ± 0.02** |
| Normal control | — | 5 | 1.34 ± 0.02** |
| Control | — | 5 | 1.43 ± 0.01 |
| Compound of Example 14 | 0.1 | 5 | 1.34 ± 0.02** |
| Compound of Example 14 | 0.3 | 5 | 1.21 ± 0.01** |
| Compound of Example 5 | 0.1 | 5 | 1.12 ± 0.01** |
| Compound of Example 5 | 0.3 | 5 | 0.97 ± 0.02** |
| Normal Control | — | 5 | 1.36 ± 0.01** |
| Control | — | 5 | 1.45 ± 0.02 |
| Compound of Example 9 | 0.1 | 5 | 1.31 ± 0.01** |
| Compound of Example 9 | 0.3 | 5 | 1.19 ± 0.01** |
| Compound of Example 10 | 0.1 | 5 | 1.35 ± 0.01** |
| Compound of Example 10 | 0.3 | 5 | 1.22 ± 0.01** |
| Normal control | — | 5 | 1.35 ± 0.02** |
| Control | — | 5 | 1.44 ± 0.01 |
| Compound of Example 11 | 1.0 | 5 | 1.35 ± 0.02** |
| Normal control | — | 5 | 1.38 ± 0.01** |
| Control | — | 5 | 1.48 ± 0.02 |
| Compound of Example 7 | 0.3 | 5 | 1.40 ± 0.02** |
| Compound of Example 7 | 1.0 | 5 | 1.29 ± 0.01** |
| Compound of Example 6 | 0.3 | 5 | 1.33 ± 0.03** |
| Compound of Example 6 | 1.0 | 5 | 1.12 ± 0.03** |
| Normal control | — | 5 | 1.38 ± 0.01** |
| Control | — | 5 | 1.49 ± 0.00 |
| SCT | 0.3 IU | 5 | 1.07 ± 0.02** |

Note: Mean value ± S.E.
*: $P < 0.05$
**: $P < 0.01$ (2) PTH-Induced Hypercalcemia in Rats Methods PTH (human PTH 1-34, 30 μg/kg) was intravenously injected to rats (Wistar, male, about 3-week-old). The blood was collected 45 min. after PTH injection. Ionized calcium ($CA^{++}$) in the serum was measured with a $Ca^{++}$ meter.

Test compounds were subcutaneously or orally administered three days before PTH injection. Results are expressed as mean ±S.E. Statistical significance of the values was analyzed using One-Way ANOVA test (*: $p<0.05$, **: $p<0.01$).

Results

PTH elevated serum $Ca^{++}$ level probably by stimulation of calcium release from the bone. Bisphosphonates, the compound of Example 5 (hereinafter, YM-21175-1) and APD*, were dose-dependently inhibited the increase of serum $Ca^{++}$ level when they were subcutaneously or orally administered to the rats 3 day before PTH injection. YM-21175-1 was about 10 times more potent than APD in both cases of subcutaneous or oral administration.

TABLE 2

Effects of YM-21175-1 and APD on PTH-induced hypercalcemia in rats

|  | Dose (mg/kg) | N | Serum Ca$^{++}$ (m mole/l) |
|---|---|---|---|
| normal (−PTH) | — | 5 | 1.42 ± 0.02 |
| control (+PTH) | — | 5 | 1.49 ± 0.02 |
| APD | 0.03 sc | 5 | 1.49 ± 0.02 |
|  | 0.1 sc | 5 | 1.46 ± 0.01 |
|  | 0.3 sc | 5 | 1.41 ± 0.02* |
| APD | 30 po | 5 | 1.50 ± 0.02 |
|  | 100 po | 5 | 1.42 ± 0.02 |
|  | 300 po | 5 | 1.22 ± 0.02** |
| YM-21175-1 | 0.01 sc | 5 | 1.44 ± 0.02 |
|  | 0.03 sc | 5 | 1.36 ± 0.02** |
|  | 0.1 sc | 5 | 1.15 ± 0.01** |
| normal (−PTH) | — | 5 | 1.35 ± 0.02 |
| control (+PTH) | — | 5 | 1.45 ± 0.02 |
| YM-21175-1 | 10 po | 5 | 1.37 ± 0.02 |
|  | 30 po | 5 | 1.23 ± 0.05** |
|  | 100 po | 5 | 1.05 ± 0.04** |

*APD (Ciba-Geigy); H$_2$NCH$_2$CH$_2$C(PO$_3$H$_2$)$_2$
OH (a medicine for treating bone Paget available on market)

(3) Disuse Atrophy of Bone Induced by Neurectomy in Rats

Methods

Rats (Wistar, male, 6-week-old) were neurectomized at brachial plexisus so that their left forelimbs were disused. Two weeks later, left humerus was removed. The soft tissue around the bone was cleaned off and the bone was dehydrated and defatted with alcohol and acetone successively. Dry weight of the bones was measured.

Compounds were orally administered once a day for 2 weeks. Results were expressed as mean ±S.E. Statistical significance of the values was analyzed using One-Way ANOVA test (*: p<0.05, **: p<0.01).

Results

The dry weight of the denerved humerus was significantly decreased as compared with that of the sham-operated one. Oral administration of bisphosphonates, YM-21175-1 and APD, exhibited the dose-dependent inhibition of dry weight loss in the denerved humerus. YM-21175-1 was about 30 times superior to APD.

TABLE 3

Effects of YM-21175-1 and APD on disuse atrophy of bone induced by neurectomy in rats

|  | Dose (mg/kg) | N | dry wt (mg) |
|---|---|---|---|
| sham operated | — | 6 | 154 ± 3** |
| control | — | 6 | 113 ± 2 |
| APD | 10 | 5 | 126 ± 3 |
|  | 30 | 5 | 128 ± 4* |
|  | 100 | 6 | 135 ± 2** |
| YM-21175-1 | 0.3 | 6 | 126 ± 2 |
|  | 1 | 6 | 132 ± 6** |
|  | 3 | 6 | 135 ± 3** |
|  | 10 | 6 | 150 ± 4** |

(4) Adjuvant-Induced Arthritic in Rats

Methods

A suspension of dead bacilli in oil was intradermally injected into left hind paws of rats (Lewis, male, 5-week-old). Compounds were orally given daily for 5 weeks, starting from the day of injection of the adjuvant. Thickness of the left hind foot was measured and left femur was removed at the next day of last dosing. The bones were dehydrated and defatted, and then dry weight of them was measured. They were measured again after they were ashed.

Bone mineral content (BMC) was calculated as ash wt/dry wt. Results were expressed an mean ±S.E. (N=6). Statistical significance of the values was analyzed using One-Way ANOVA test (**: p<0.01).

Results

Adjuvant-induced arthritis is one of popularly used models for rheumatoid arthritis in humans. Arthritic rats induced by injection of the adjuvant show not only the swelling of the foot but also decrease of BMC, which is supposed to be caused by increase of bone resorption and/or disuse of hindlimbs.

Indomethacin 1 mg/kg markedly inhibited the swelling of hindlimbs. It also inhibited the decrease of BMC as a result of the inhibition of development the arthritis. YM-21175-1 inhibited the swelling only at high doses but decrease of BMC at 1 mg/kg. Therefore there is the probability of a difference of the inhibitory action between indomethacin and YM-21175-1. YM-21175-1 was more effective than APD.

TABLE 4

Effects of YM-21175-1 and APD on adjuvant-induced arthritis in rats

|  | dose (mg/kg) | N | thickness (mm) | ash wt/dry wt (%) |
|---|---|---|---|---|
| normal | — | 6 | 6.4 ± 0.0 | 54.8 ± 0.1** |
| control | — | 6 | 13.5 ± 0.1 | 49.5 ± 0.4 |
| indomethacin | 1 | 6 | 7.6 ± 0.1** | 52.3 ± 0.2** |
| APD | 1 | 6 | 12.1 ± 0.6 | 50.4 ± 0.3 |
|  | 3 | 6 | 11.6 ± .07 | 51.2 ± 0.4** |
|  | 10 | 6 | 10.8 ± 0.6** | 52.1 ± 0.5** |
|  | 30 | 6 | 12.1 ± 0.3 | 53.3 ± 0.3** |
|  | 100 | 6 | 9.3 ± 0.3** | 56.6 ± 0.3** |
| YM-21175-1 | 0.3 | 6 | 12.3 ± 0.6 | 50.7 ± 0.6 |
|  | 1 | 6 | 11.7 ± 0.1 | 52.1 ± 0.8** |
|  | 3 | 6 | 12.3 ± 0.8 | 53.1 ± 0.4** |
|  | 10 | 6 | 10.5 ± 0.7** | 55.9 ± 0.3** |
|  | 30 | 5 | 9.5 ± 0.2** | 57.6 ± 0.3** |

The inhibitory effect of YM-21175-1 on bone loss was compared with APD. As results in three kinds of experiments, YM-21175-1 is thought to be useful in the treatment of osteoporosis, rhumatoid arthritis and other diseases in which the bone resorption was accelerated, and besides YM-21175-1 is concluded to be more potent than APD.

From the test results, the compounds of the present invention were demonstrated to have an excellent action for reducing the amount of serum calcium. Accordingly, it is confirmed that the compounds of the present invention have a bone-resorption inhibitory action. As diseases considered to be caused by an excessive bone-resorption, there may be mentioned Paget's disease, hypercalcemia, metastatic osteocarcinoma, and osteopsathrosis. Further, sthenic bone resorption to follow inflammatory arthritides such as chronic rheumatoid arthritis is an important problem from a clinical point of view. The compounds provided by the present invention can be used as remedial medicines for these diseases to inhibit the bone resorption and prevent the reduction of the bone amount or prevent the rising of the serum calcium value caused by the sthenic bone resorption or lower the value.

The compounds (I) of the present invention and their salts can be blended with any optional pharmaceutically acceptable carrier, vehicle, attenuant, etc. to be formed into medical composition, such as tablets, capsules, powder, granules, pills, etc. for oral administration of injection, syrup, suppositories, ointment, etc. for non-oral administration. The amount of the dose of the compounds (I) of the present invention is, although varying in accordance with the administration route, patient's symptom, etc., generally from 1 mg/day/adult to 1 g/day/adult for oral administration, and from 0.1 to 10 mg/day/adult for non-oral administration.

Prescription Example

Examples for prescription of the compound of the present invention as a drug will be mentioned below.

| (1) Tablet: | |
|---|---|
| Compound of Example 8 | 5 mg |
| Lactose | 119 mg |
| Corn Starch | 67 mg |
| Hydroxypropyl Cellulose | 4 mg |
| Calcium Carboxymethyl Cellulose | 4 mg |
| Magnesium Stearate | 1 mg |
| Total | 200 mg |

5 g of the compound of Example 8, 119 g of lactose and 67 g of corn starch were uniformly blended, 40 ml of an aqueous 10% (w/w) hydroxypropyl cellulose solution was added thereto, and the resulting mixture was wet-granulated. The granules thus obtained were blended with 4 g of calcium carboxymethyl cellulose and 1 g of magnesium stearate, and the resulting mixture is formed into tablets each having a weight of 200 mg/tablet.

| (2) Capsule: | |
|---|---|
| Compound of Example 8 | 5 mg |
| Crystalline Cellulose | 50 mg |
| Crystalline lactose | 144 mg |
| Magnesium Stearate | 1 mg |
| Total | 200 mg |

The above-mentioned ingredients were blended each in an amount of 1000 times of the above-mentioned amount and encapsulated in gelatin capsules each containing 200 mg of the mixture per one capsule.

Preparation Examples

The process for manufacturing the compounds of the present invention will be explained in the following examples.

EXAMPLE 1

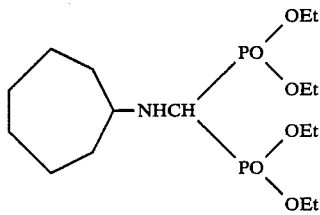

A mixture of 4.0 g of cycloheptylamine, 6.27 g of ethyl ortho-formate and 19.5 g of diethylphosphite was heated at 150° C. with stirring for 1.5 hours. After cooling, the reaction solution was concentrated under reduced pressure to eliminate ethyl ortho-formate and diethylphosphite which were not reacted. Then, the residue was purified on silica gel column chromatography (methanol/chloroform=1/49) to give 9.0 g of tetraethyl (cycloheptylamino)methylenebis(phosphonate) as a pale yellow oil.

The physico-chemical characteristics of this product are as follows:

(i) Mass Spectrum (FAB Mass) 400 (M$^+$+1)

(ii) Nuclear Magnetic Resonance Spectrum ($\delta$ value, in CDCl$_3$)

| 1.32 | (12H, OCH$_2$C$\underline{H}_3$ × 4) |
|---|---|
| 1.20~2.08 | (12H, H methylene in cycloheptyl group) |
| 2.96 | (1H, —N$\underline{H}$—⟨cycloheptyl with H⟩) |
| 3.36 | (1H, —NHC$\underline{H}$—) |
| 4.00~4.40 | (8H, —OC$\underline{H}_2$CH$_3$ × 4) |

In the same manner as Example 1, the following compounds were prepared.

EXAMPLE 2

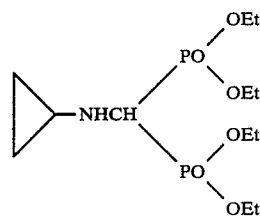

Tetraethyl (cyclopropylamino)methylenebis(phosphonate) Yellow oil (i) Mass Spectrum (FAB Mass) 344 (M$^+$+1)

(ii) Nuclear Magnetic Resonance Spectrum ($\delta$ value, in CDCl$_3$)

| 0.36~0.56 | (4H, —⟨C$\underline{H}_2$/C$\underline{H}_2$⟩) |
|---|---|
| 1.35 | (12H, OCH$_2$C$\underline{H}_3$ × 4) |
| 1.94 | (1H, —N$\underline{H}$—) |
| 2.65 | (1H N—⟨cyclopropyl⟩ $\underline{H}$) |
| 3.40 | (1H, —NC$\underline{H}$—) |
| 3.96~4.40 | (8H, —OC$\underline{H}_2$CH$_3$ × 4) |

EXAMPLE 3

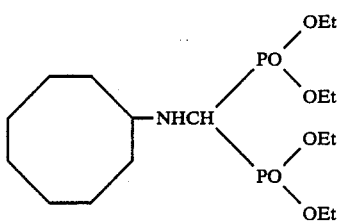

Tetraethyl (cyclooctylamino)methylenebis(phosphonic acid)

(i) Mass Spectrum (FAB Mass) 414 (M+ +1)
(ii) Nuclear Magnetic Resonance Spectrum (δ value, in CDCl₃)

| | |
|---|---|
| 1.34 | (12H, —OCH₂C$\underline{H}$₃ × 4) |
| 1.20~2.40 | (14H, H methylene in cyclooctyl group) |
| 3.04 | (1H, —N$\underline{H}$—, cyclooctyl) 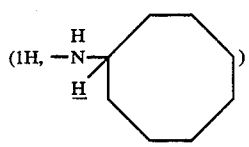 |
| 3.36 | (1H, —NHC$\underline{H}$—) |
| 4.00~4.48 | (8H, —OC$\underline{H}$₂CH₃ × 4) |

EXAMPLE 4

| | |
|---|---|
| 0.92 | (3H, CH₃-cyclohexyl) |
| 1.34 | (12H, —OCH₂C$\underline{H}$₃ × 4) |
| 1.20~2.40 | (9H, cyclohexyl H's) 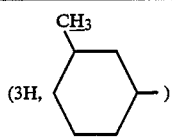 |
| 2.80 | (1H, —N$\underline{H}$—) 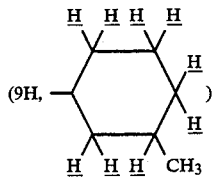 |
| 3.44 | (1H, —NC$\underline{H}$—) |
| 4.00~4.42 | (8H, —OC$\underline{H}$₂CH₃ × 4) |

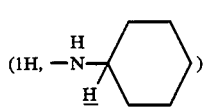

Tetraethyl [(3-methylcyclohexyl)amino]methylenebis(phosphonate)

(i) Mass Spectrum (FAB Mass) 400 (M+ +1)
(ii) Nuclear Magnetic Resonance Spectrum

EXAMPLE 5

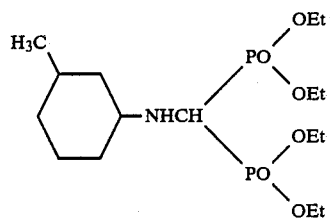

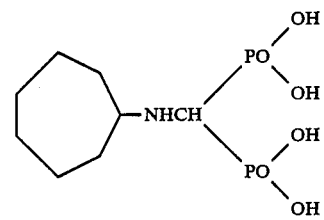

4.0 g of tetraethyl (cycloheptylamino)methylenebis(phosphonate) was dissolved in 40 ml of concentrated hydrochloric acid and heated under reflux for 2.5 hours. After cooling, the reaction solution was concentrated under reduced pressure to eliminate hydrochloric acid. Then, 30 ml of purified water was added to the residue and the mixture was again concentrated under reduced pressure. The oily product thus obtained was solidified by methanol and acetone and subject to the filtration. The residue was washed with acetone to give 2.5 g of (cycloheptylamino)methylenebis(phosphonic acid) as a white solid.

This had the following phosico-chemical properties:
(i) Mass Spectrum (FAB Mass) 288 (M+ +1)
(ii) Elementary Analysis (C₈H₁₉NO₆P₂)

| | C | H | N | P |
|---|---|---|---|---|
| Calculated (%): | 33.46 | 6.67 | 4.88 | 21.57 |
| Found (%): | 33.27 | 6.40 | 4.87 | 21.54 |

(iii) m.p.: 232° to 233° C. (Recrystallization from MeOH-H₂O)

In the same manner as Example 5, the following compounds were prepared.

EXAMPLE 6

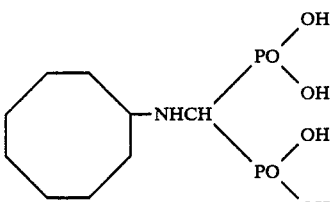

(Cyclooctylamino)methylenebis(phosphonic acid)
(i) Mass Spectrum (FAB Mass) 302 (M+ +1)
(ii) Elementary Analysis (C₉H₂₁NO₆P₂)

| | C | H | N | P |
|---|---|---|---|---|
| Calculate (%): | 35.89 | 7.03 | 4.65 | 20.57 |

-continued

| | C | H | N | P |
|---|---|---|---|---|
| Found (%): | 35.87 | 6.82 | 4.69 | 20.49 |

(iii) m.p. (°C.) 228 to 229 (Not purified)

EXAMPLE 7

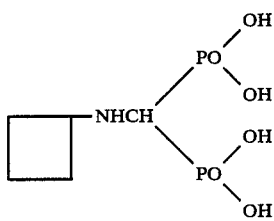

(Cyclobutylamino)methylenebis(phosphonic acid)
(i) Elementary Analysis ($C_5H_{13}NO_6P_2$)

| | C | H | N |
|---|---|---|---|
| Calculated (%): | 24.50 | 5.35 | 5.71 |
| Found (%): | 24.41 | 5.23 | 5.66 |

(ii) m.p. (°C.) 256 to 258 (Recrystallization from methanol)

EXAMPLE 8

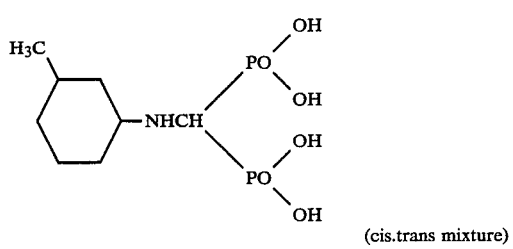

(cis.trans mixture)

[(3-methylcyclohexyl)amino]methylenebis(phosphonic acid)
(i) Mass Spectrum (FAB Mass) 288 ($M^+ + 1$)
(ii) Elementary Analysis ($C_8H_{19}NO_6P_2 \cdot 0.2H_2O$)]

| | C | H | N | P |
|---|---|---|---|---|
| Calculated (%): | 33.04 | 6.72 | 4.81 | 21.30 |
| Found (%): | 32.88 | 6.47 | 4.77 | 21.32 |

(iii) m.p. (°C.) 220 to 221 (Not purified)

EXAMPLE 9

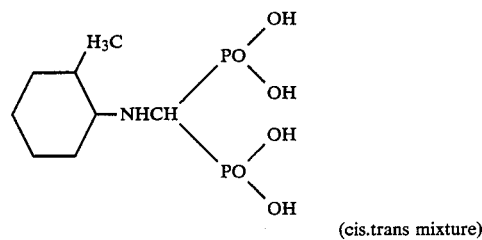

(cis.trans mixture)

[(2-methylcyclohexyl)amino]methylenebis(phosphonic acid)

(i) Elementary Analysis ($C_8H_{19}NO_6P_2$)

| | C | N | N |
|---|---|---|---|
| Calculated (%): | 33.46 | 6.67 | 4.88 |
| Found (%): | 33.07 | 6.39 | 4.86 |

(ii) m.p. (°C.) 238 to 240 (Recrystallization from methanol-acetone)

EXAMPLE 10

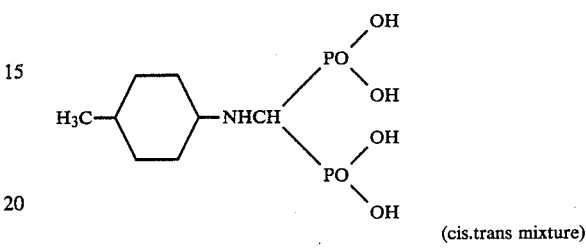

(cis.trans mixture)

[(4-methylcyclohexyl)amino]methylenebis(phosphonic acid)
(i) Elementary Analysis ($C_8H_{19}NO_6P_2$)

| | C | N | N |
|---|---|---|---|
| Calculated (%): | 33.46 | 6.67 | 4.88 |
| Found (%): | 33.13 | 6.41 | 4.75 |

(ii) m.p. (°C.) 255 to 258 (Recrystallization from methanol-water)

EXAMPLE 11

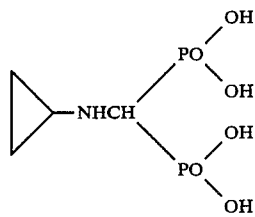

1.28 g of tetraethyl (cyclopropylamino)methylenebis(phosphonate) was dissolved in 13 ml of 25% hydrogen bromide acetic acid solution and the mixture was stirred at 45° C. for 2 hours. The reaction solution was concentrated under reduced pressure, and 20 ml of purified water was added to the residue. Then, the mixture was again concentrated under reduced pressure. The oily product thus obtained was solidified by methanol and acetone and subjected to the filtration. The solid was washed with acetone to give 0.42 g of (cyclopropylamino)methylenebis(phosphonic acid) as a white solid.

The physico-chemical characteristics of this product are as follows:
(i) Mass Spectrum (FAB Mass) 232 ($M^+ + 1$)
(ii) Elementary Analysis ($C_4H_{11}NO_6P_2 \cdot 0.2H_2O$)

| | C | H | N | P |
|---|---|---|---|---|
| Calculated (%): | 30.47 | 4.89 | 5.96 | 26.39 |
| Found (%): | 20.45 | 4.73 | 5.83 | 26.33 |

EXAMPLE 12

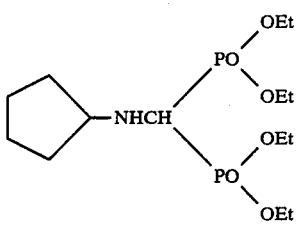

The mixture solution of 3.0 g of cyclopentylamine, 6.2 g of ethyl ortho-formate and 19.4 g of diethylphosphite was heated at 150° C. with stirring for 1.5 hours. After cooling, the reaction solution was concentrated under reduced pressure to eliminate ethyl orthoformate and diethylphosphite which were not reacted. Then, the residue was purified on a silica gel column chromatography (methanol/chloroform=1/49) to give 10.7 g of tetraethyl (cyclopentylamino)methylenebis(phosphonate) as a pail yellow oil.

The pysico-chemical properties of this product are as follows:

(i) Mass Spectrum (FAB Mass): 372 (M$^+$+1)

(ii) Nuclear Magnetic Resonance Spectrum ($\delta$ value, in CDCl$_3$)

| 1.34 | (12H, OCH$_2$C$\underline{H}$$_3$ × 4) |
|---|---|
| 1.42~2.00 | (8H, H methylene cyclopentyl group) |
| 3.30 | (1H, —NHC$\underline{H}$—) |
| 3.48 | 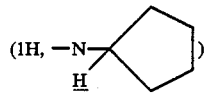 (1H, —N—) |
| 4.00~4.36 | (8H, —OC$\underline{H}$$_2$CH$_3$ × 4) |

In the same manner as Example 12, the following compounds were prepared.

EXAMPLE 13

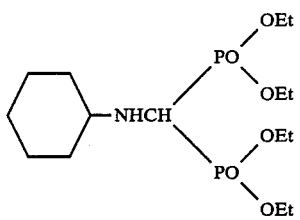

Tetraethyl (cyclohexylamino)methylenebis(phosphonate)

(i) Mass spectrum (FAB Mass) 386 (M$^+$+1)

(ii) Nuclear Magnetic Resonance Spectrum ($\delta$ value in CDCl$_3$)

| 1.32 | (12H, —OCH$_2$C$\underline{H}$$_3$ × 4) |
|---|---|
| 1.2~2.0 | (10H, H methylene in a cyclohexyl group) |
| 2.90 | 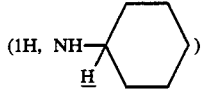 (1H, NH) |
| 3.44 | (1H, NHC$\underline{H}$) |
| 4.00~4.40 | (8H, —OC$\underline{H}$$_2$CH$_3$ × 4) |

EXAMPLE 14

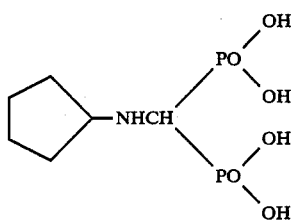

8.0 g of tetraethyl (cyclopentyl amino)methylenebis(phosphonate) was dissolved in 80 ml of concentrated hydrochloric acid and the mixture was heated under reflux for 2.5 hours. After cooling, the reaction solution was concentrated under reduced pressure to eliminate hydrochloric acid. 70 ml of purified water was added to the residue and the mixture was again concentrated under reduced pressure. The obtained product in the form of oil was solidified by acetone and acetonitrile and subjected to the filtration. The product was recrystallized from water-methanol to give 3.6 g of (cyclopenthylamino)methylenebis(phosphonic acid) as white crystals.

The physico-chemical properties of this product are as follows:

(i) Mass Spectrum (FAB Mass): 260 (M$^+$+1)

(ii) Elementary Analysis (C$_6$H$_{15}$NO$_6$P$_2$.0.1H$_2$O)

|  | C | H | N | P |
|---|---|---|---|---|
| Calculated (%): | 27.62 | 5.87 | 5.37 | 23.74 |
| Found (%): | 27.42 | 5.67 | 5.48 | 23.66 |

In the same manner as Example 14 the following compound was prepared.

EXAMPLE 15

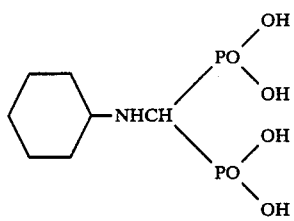

(Cyclohexylamino)methylenebis(phosphonic acid)

(i) Mass Spectrum (FAB Mass) 274 (M$^+$+1)

(ii) Elementary Analysis (C$_7$H$_{17}$NO$_6$P$_2$)

|  | C | H | N | P |
|---|---|---|---|---|
| Calculatd (%): | 30.78 | 6.27 | 5.13 | 22.68 |
| Found (%): | 30.48 | 6.11 | 5.16 | 22.17 |

(iii) m.p. (°C.) 267° to 269° C. (Not purified)

We claim:

1. (Cycloalkylamino)methylenebis(phosphonic acid) or a lower alkyl ester thereof represented by the general formula:

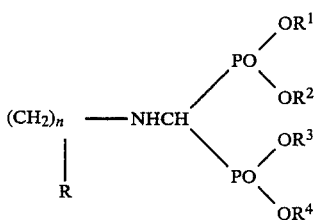

in which, R, $R^1$, $R^2$, $R^3$ and $R^4$ represent a hydrogen atom or a lower alkyl group, n represents an integer from 3 to 10 but R represents a lower alkyl group when n is 5 or 6; or a pharmaceutically acceptable salt thereof.

2. (Cycloalkylamino)methylenebis(phosphonic acid), a lower alkyl ester thereof or a pharmaceutically acceptable salt thereof set forth in claim 1, wherein said compound is (cycloheptylamino)methylenebis(phosphonic acid).

* * * * *

UNITED STATES PATENT AND TRADEMARK OFFICE
CERTIFICATE OF CORRECTION

PATENT NO. : 4,970,335

DATED : November 13, 1990

INVENTOR(S) : Yasuo Isomura, et al

It is certified that error appears in the above-identified patent and that said Letters Patent is hereby corrected as shown below:

Column 9, line 37: after "Example 4" insert the following:

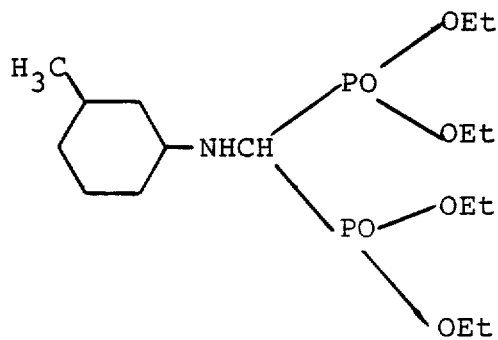

Tetraethyl [(3-methylcyclohexyl)amino]methylenebis(-phosphonate)

(i) Mass Spectrum (FAB Mass) 400 ($M^{+}+1$)

(II) Nuclear Magnetic Resonance Spectrum

Column 9, delete lines 64-67

Column 10, delete the formula at line 5

Column 12, after the last line insert --(iii) m.p. (°C) 214 to 216°C (Not purified)--

UNITED STATES PATENT AND TRADEMARK OFFICE
CERTIFICATE OF CORRECTION

PATENT NO.   :   4,970,335

DATED        :   November 13, 1990

INVENTOR(S)  :   Yasuo Isomura, et al

It is certified that error appears in the above-identified patent and that said Letters Patent is hereby corrected as shown below:

Column 14, line 40:   insert --(iii)  m.p. (°C) 228 to 229°C--

Column 15:  that portion of the formula reading

"$(CH_2)_n\!\!-\!\!\underset{R}{|}$"   should read   -- 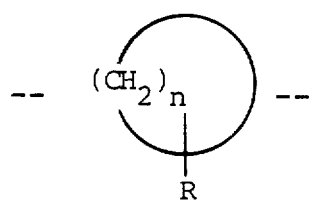 --

Signed and Sealed this

Nineteenth Day of May, 1992

Attest:

DOUGLAS B. COMER

*Attesting Officer*    Acting Commissioner of Patents and Trademarks